(12) United States Patent
Della Valle et al.

(10) Patent No.: US 11,491,122 B2
(45) Date of Patent: Nov. 8, 2022

(54) USE OF A COMBINATION OF ADELMIDROL AND HYALURONIC ACID IN THE TREATMENT OF PAIN CAUSED BY OSTEOARTHRITIS AND EPITHELIAL DYSFUNCTIONS

(71) Applicant: Epitech Group S.p.A., Milan (IT)

(72) Inventors: Maria Federica Della Valle, Milan (IT); Francesco Della Valle, Milan (IT); Vincenzo Di Marzo, Milan (IT); Stefania Petrosino, Milan (IT); Barbara Costa, Milan (IT); Gabriele Marcolongo, Milan (IT); Daniele Grassi, Milan (IT)

(73) Assignee: Epitech Group S.p.A., Milan (IT)

( * ) Notice: Subject to any disclaimer, the term of this patent is extended or adjusted under 35 U.S.C. 154(b) by 54 days.

(21) Appl. No.: 16/374,912

(22) Filed: Apr. 4, 2019

(65) Prior Publication Data

US 2019/0224145 A1 Jul. 25, 2019

Related U.S. Application Data

(63) Continuation of application No. 15/482,129, filed on Apr. 7, 2017, now abandoned, which is a continuation of application No. 14/793,165, filed on Jul. 7, 2015, now abandoned.

(30) Foreign Application Priority Data

Jul. 8, 2014 (IT) .......................... MI2014A001245

(51) Int. Cl.
| | |
|---|---|
| *A61K 31/16* | (2006.01) |
| *A61K 45/06* | (2006.01) |
| *A61K 31/164* | (2006.01) |
| *A61K 31/201* | (2006.01) |
| *A61K 31/421* | (2006.01) |
| *A61K 31/728* | (2006.01) |
| *A61K 36/062* | (2006.01) |
| *A61K 36/28* | (2006.01) |

(52) U.S. Cl.
CPC ............ *A61K 31/16* (2013.01); *A61K 31/164* (2013.01); *A61K 31/201* (2013.01); *A61K 31/421* (2013.01); *A61K 31/728* (2013.01); *A61K 36/062* (2013.01); *A61K 36/28* (2013.01); *A61K 45/06* (2013.01)

(58) Field of Classification Search
CPC combination set(s) only.
See application file for complete search history.

(56) References Cited

U.S. PATENT DOCUMENTS

2006/0257510 A1* 11/2006 Della Valle .......... A61K 31/047 424/737

FOREIGN PATENT DOCUMENTS

WO WO 2013/121449 * 8/2013

OTHER PUBLICATIONS

Filippis (Adelmidrol, a palmitoylethanolamide analogue, reduces chronic inflammation in a carrageenin-granuloma model in rats, J. Cell. Mol. Med. vol. 13, No. 6, 2009 pp. 1086-1095).*
Berenbaum (Osteoarthritis as an inflammatory disease (osteoarthritis is not osteoarthrosis!), Osteoarthritis and Cartilage 21 (2013) 16-21).*
Yu (Anti-inflammatory effects of essential oil in *Echinacea purpurea* L., Pak J Pharm Sci. Mar. 2013;26(2):403-8. (Abstract only)).*

* cited by examiner

*Primary Examiner* — Kathrien A Cruz
(74) *Attorney, Agent, or Firm* — MacMillan, Sobanski & Todd, LLC

(57) ABSTRACT

Described herein is the use of Adelmidrol in the treatment of epithelial dysfunctions. In particular, described herein is Adelmidrol for use in the treatment of epithelial tissue dysfunctions in a human being or animal, wherein said Adelmidrol causes an increase of the endogenous levels of Palmitoylethanolamide without inhibiting the activity of the Palmitoylethanolamide-degrading FAAH and NAAA enzymes.

6 Claims, 2 Drawing Sheets

*\*P<0.01 vs non OA, °°P<0.01 vs OA (ANOVA; Tukey's test)

USE OF A COMBINATION OF ADELMIDROL AND HYALURONIC ACID IN THE TREATMENT OF PAIN CAUSED BY OSTEOARTHRITIS AND EPITHELIAL DYSFUNCTIONS

CROSS-REFERENCE TO RELATED APPLICATIONS

This is a continuation of U.S. Ser. No. 15/482,129 filed Apr. 7, 2017, still pending, which is a continuation application of U.S. Ser. No. 14/793,165, filed on Jul. 7, 2015, now abandoned; which claims priority to Italian Application Number MI2014A001245, filed on Jul. 8, 2014. The entire disclosures of the aforementioned applications are expressly incorporated herein by reference for all purposes.

DESCRIPTION

Technical Field of Invention

The object of the present invention is Adelmidrol in the treatment of epithelial dysfunctions.

Background Art

Palmitoylethanolamide (PEA) is an endogenous lipid N-acylamidic substance of which an effect on neuroinflammation and pain has been widely demonstrated [Calignano A. et al *Europ. J. Pharmacol.* 2001; 419:191-198; Skaper S. D. et al *Mol Neurobiol.* 2013; 48:340-352; Skaper S. D. et al. *Inflammopharmacology.* 2014; 22:79-94]. On the pharmacological level, the increase in the endogenous levels of PEA is currently considered important to determine the control of the neuroinflammation and pain mechanism due to different etiopathogenetic causes and associated with many diseases both of human beings and animals [Petrosino S. et al *WSAVA/FECAVA World Small Animal Congress* 2008; Richardson D. et al. Arthritis Research & Therapy 2008; 10 (2); R43; Ghafouri N. et al *PLoS ONE* 2011; 6(11); Naccarato M. et al *Lipids in Health and Disease* 2010; 9:47]. Two different pharmacological methods have currently been suggested to obtain this increase.

The first method is based on the systemic oral or sublingual administration of PEA: in this case, PEA must be administered in micronized (particle size in the range between 2 and 10 microns) or ultra-micronized (particle size in the range between 0.8 and 6 microns) form due to the high insolubility in water of the lipid molecule [EP 1207870 B1; WO 2011/027373 A1].

On the other hand, the second method is based on the inhibition of the activity of the specific PEA-degrading enzyme activity, i.e. FAAH (Fatty Acid Amide Hydrolase) and NAAA (N-Acylethanolamine Acid Amidase); this inhibition was obtained with the systemic administration of synthetic inhibitors of said hydrolases [Piomelli D. et al *CNS Drug Reviews* 2006; 12:21-38; Fiasella A. *Chem Med Chem* 2014 Epub of Print] able to block the degradation of PEA. However, this method implies a serious problem since blocking the degradation of PEA through the block of specific degradation enzymes corresponds to preventing reuse, which is essential, of the PEA components, ethanolamine and palmitic acid, needed to return the phospholipid from which PEA is biologically synthesized "on demand" to the cell, through the phospholipid synthesis. There is also the problem that, while the systemic oral administration of PEA in micronized or ultramicronized form has been found to be effective and safe [Skaper S. D. et al *Inflammopharmacol.* 2014; 22:79-94; Esposito E. et al., *Mini Rev Med Chem.* 2013; 13:237-55], the topical use, in the form of a cream or solution, is very difficult and poorly effective because of the difficulty of producing, in this manner, pharmacologically effective amounts of PEA as a result of the high hydrophobicity of this important lipid molecule.

Adelmidrol is a synthetic N-acylamidic molecule as well (N,N'-Bis(2-hydroxyethyl)nonandiamide) with a high solubility in water as well as a good solubility in lipids.

SUMMARY OF INVENTION

The inventors of the present patent have surprisingly found that Adelmidrol, when brought in contact with epithelial cells such as keratinocytes, is able to cause an important increase of the endogenous levels of PEA while not interfering with the activity of the PEA-degrading enzymes (FAAH and/or NAAA). This discovery allows an effective pharmacological action on external (skin, mucocutaneous genital tissues, oral mucosa) and/or internal epithelia (bladder urothelium, ureter mucosa, mucous membranes of the seminal vesicles, mucous membranes of the digestive system, endothelial layer of synovial membranes, mucous membranes of the respiratory tract), with suitable pharmaceutical forms for the various uses, on diseases of the epithelia of different organs, both in human beings and in animals.

It may also be useful to enhance the activity of Adelmidrol on increasing the local levels of Palmitoylethanolamide by associating the same Adelmidrol with substances capable of modulating (but not blocking) the activity of PEA-degrading enzymes. In particular, PEA Oxazoline, described in the international application published with number WO 2013/121449 A1, may be used.

Therefore, an object of the present invention therefore is Adelmidrol for use in the treatment of epithelial tissue dysfunctions in a human being or animal.

A further object of the invention is a pharmaceutical formulation for use in the treatment of epithelial tissue dysfunctions in a human being or animal, the formulation containing Adelmidrol, optionally in association with an active ingredient selected from the group consisting of an oxazoline derivative of Palmitoylethanolamide, an antimicrobial agent, trans-traumatic acid, and hyaluronic acid or derivatives thereof.

The invention is defined by the appended claims.

Further features and advantages of the invention will become apparent from the following description of preferred embodiments thereof, provided by way of non-limiting example.

DETAILED DESCRIPTION OF THE INVENTION

Figure 1:
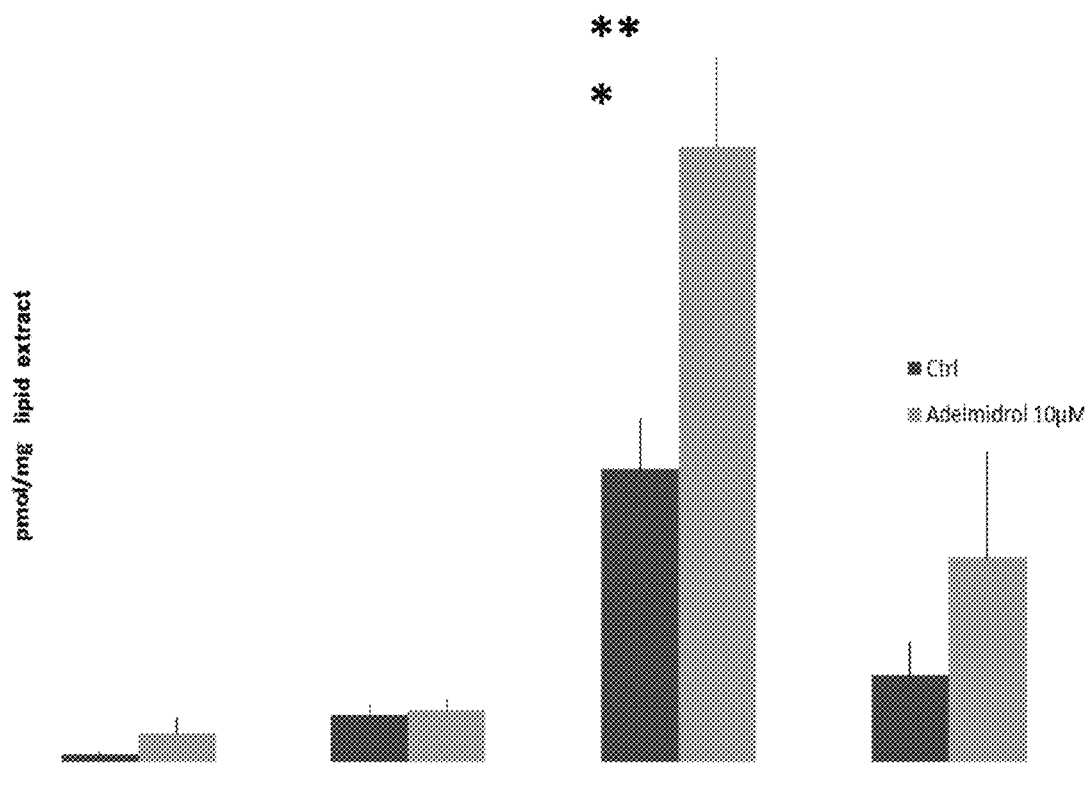
FIG. 1 shows the endogenous levels of AEA, 2-AG, PEA and OEA in HaCaT cells stimulated for 24 hours with 10 μM Adelmidrol. Ctrl (n=6) vs Adelmidrol 10 μM (n=6). $P<0.0001$ (***)

The invention relates to Adelmidrol for use in the treatment of epithelial tissue dysfunctions in a human being or animal.

Adelmidrol is the International Non-proprietary Name (INN) of a synthetic derivative of azelaic acid, a naturally-occurring saturated dicarboxylic acid. In fact, azelaic acid has been found in the human body and its plasma levels are in the range between 20-80 ng/ml.

Chemically, Adelmidrol is N,N'-bis(2-hydroxyethyl) nonandiamide; the molecule has an amphiphile behavior as it has both hydrophilic and lipophilic properties able to promote solubility both in water and in organic solvents. These features, combined with the possibility of hot-sterilizing solutions containing Adelmidrol, make the molecule highly suitable for topical application on external surfaces and internal epithelia.

Epithelial dysfunctions treated with Adelmidrol according to the present invention are preferably selected from the group consisting of: oropharyngeal and esophageal Dysphagia with different etiology; gastroesophageal reflux; Cricopharyngeal Achalasia; esophageal Achalasia; stomatites with different etiology; Presbiphagia in the elderly; feline gingivostomatitis; periodontal disease also related to endodontics/orthodontics and dental implantology interventions; Burning Mouth Syndrome (BMS); Eyelid Edema; Blepharitis, Blepharoconjunctivitis; inward turning (entropion) and eversion (ectropion) of the eyelid; keratitis and keratitoconjunctivitis with different etiology (e.g., superficial punctate keratitoconjunctivitis); corneal lesions with different etiology; quali-quantitative alterations of the tear film; Dacryocystitis; Uveitis; Glaucoma; diseases of the ceruminous glands of the ear; ear hematomas in dog and cat; fly strike irritations in dog and cat; Pododermatites; Rhinites, Rhinotracheites, acute and chronic rhinopharyngites; acute and chronic Pharyngites; acute and chronic bronchites; Sinusites, Rinosinusites; bronchial asthma; Alopecia; nasal dermatoses in dog and cat; Acute and chronic sialadenites; neuropathic itch; bladder pain syndrome with different etiology attributable to alterations of the urothelium and in particular interstitial cystitis, cystitis due to systemic chemotherapeutics, cystitis due to bladder instillation of local chemotherapeutics, such as Epirubicin or Mitomycin, cystitis due to pelvic radiotherapy; chronic and/or recurrent Cystites; Gastrointestinal disorders attributable to alterations of the epithelium; Diseases of the ano-rectal segment, particularly posterior rectocele, proctites, muco-rectal prolapse, hemorrhoids, anal rhagades, perianal itching, diseases of the anal sacs in dog, and other perineal dysfunctions; small and medium vessel Vasculites and particularly granulomatous Vasculites, Vasculites due to immunocomplexes; Inflammations of the secondary sexual glands and particularly of the seminal vesicles and the seminal ducts; orofacial pain syndromes in the human and veterinary field; synovites associated with rheumatoid arthritis and osteoarthrosis.

The concentration of Adelmidrol in pharmaceutical forms for topical application (creams, gels, patches) intended for use in a human being and in an animal is in the range between 0.2% and 7.0%.

In solutions for application on internal epithelia (endovesical instillations, infusions in seminal vesicles, introduction in joint cavity, nebulizer solutions), Adelmidrol should be used in a concentration in the range between 0.3% and 5.0%.

The amounts of pharmaceutical forms for topical application (creams, gels, patches) for use both in a human being and in an animal are in the range between 0.01 and 0.5 ml per $cm^2$ of epithelium (e.g. skin, mucous membranes); thereby, the administered dose of Adelmidrol does not exceed the $LD_{50}$ of the molecule by more than 10%, which is calculated in experimental animals and by oral administration, in 2-3 g/kg body weight.

The amount of Adelmidrol to be administered in the form of solutions intended for internal epithelia (endovesical instillations, infusions in seminal vesicles, introduction in joint cavity, nebulizer solutions) is in the range between 0.5 and 20 mg/Kg body weight.

It should be considered that it may be necessary to make continual changes in the dosage depending on the patient's age and weight and on the clinical severity of the condition being treated. Finally, the exact dose and route of administration will be at the discretion of the treating physician or veterinarian.

Adelmidrol may be administered in combination with an active ingredient selected from the group consisting of an oxazoline derivative of palmitoylethanolamide, an anti-microbial agent, trans-traumatic acid and hyaluronic acid or derivatives thereof.

The anti-microbial agent is preferably selected from *Echinacea purpurea* extract, *Usnea barbata* extract, usnic acid, phytosphingosine, bronopol and mixtures thereof.

In case of combination of Adelmidrol smith hyaluronic acid and trans-traumatic acid, preferably the latter two active ingredients will be present in the sodium hyaluronate trans-traumatate double salt form.

When Adelmidrol is administered in combination with an active substance as defined above, a joint (i.e. in the same pharmaceutical formulation), separate or sequential administration may be provided.

A pharmaceutical formulation according to the invention may have the following composition by weight, the balance being related only to the active ingredients (thus, excluding carriers and excipients):

| | |
|---|---|
| Adelmidrol | 50-100% |
| Oxazoline derivative of PEA | 0-5% |
| Hyaluronic acid or derivative thereof | 0-5% |
| Trans-traumatic acid | 0-5% |
| Anti-microbial agent | 0-1% |

The treatment with Adelmidrol is topical (on external epithelia or internal epithelia).

The inventive formulation can thus contain pharmaceutically acceptable additives and excipients, selected according to the selected pharmaceutical form, such as solvents, viscous carriers, tackifying agents (acrylic polymers), buffering agents, preservatives, antioxidants, gelling agents, thickeners and so on.

Pharmaceutical formulations suitable for both human and veterinarian use can be preferably selected from: instillation solutions, solutions for inclusion in the joint capsule, gels for internal or external use, spray solutions, eye drops, creams, salves, patches and ointments.

According to the present invention, the compounds can also be formulated as rectal formulations such as suppositories, retention enemas or micro-enemas, for example containing the basic components of common suppositories such as cocoa butter or other glycerides.

In addition to the formulations described above, the compounds may also be formulated as deposition preparations. Such long-acting formulations may be administered by implantation (e.g. subcutaneously or by transdermal or intramuscular route). Therefore, for example, the compounds according to the present invention may be formulated with appropriate hydrophobic or polymeric materials (e.g. in the form of an emulsion in a suitable oil) or ion exchange resins or as minimally soluble derivatives, for example as minimally soluble salt.

The formulations described above may be prepared according to conventional methods, such as those described in Remington's Pharmaceutical Sciences Handbook, Mack Pub. Co., N.Y., USA.

EXPERIMENTAL PART

In Vitro Test on Isolated Cells

Methods

Cultured human keratinocytes, HaCaT, were grown in DMEM (Dulbecco's Modified Eagle Medium) supplemented with glutamine (2 mM), penicillin (400 U/ml), streptomycin (50 mg/ml), 10% FBS (Fetal Bovine Serum), in the presence of 5% $CO_2$ and at 37° C. Thereafter, cells plated in 6-well multi-wells ($9 \times 10^5$/well), once 70% confluence had been reached, were stimulated with Adelmidrol, 10 μM, or carrier (Ctrl, 0.05% methanol) for 24 hours in the presence of 5% $CO_2$ at 37° C. After 24 hours, the cells and the surnatants were homogenized in 5 vol. of a chloroform/methanol TRIS-HCl 50 mM pH 7.4 (2:1:1) solution containing 10 pmol of $[^2H]_8$anandamide (AEA) and 50 pmol of $[^2H]_5$2-arachidonoylglycerol (2-AG), $[^2H]_4$palmitoylethanolamide (PEA) and $[^2H]_2$oleoylethanolamide (OEA) (Bisogno et al., 1997). The organic-lipidic phase obtained from the four extractions with chloroform was subjected to purification by silica column chromatography, eluted by increasing concentrations of methanol in chloroform. The chloroform/methanol 90:10 fraction containing AEA, 2-AG, PEA and OEA was analyzed by liquid chromatography coupled to mass spectrometry using chemical ionization at atmospheric pressure (LC-APCI-MS) (Marsicano et al., 2002). The equipment used includes a Shimadzu HPLC (LC-10ADVP) coupled with a Shimadzu spectrometer (LCMS-2010) via a Shimadzu APCI interface. The ionization source temperature is 400° C. and a Phenomenex reverse phase HPLC column (C-18, 5 microns, 150×4.6 mm) is used. The mobile phase, consisting of a mixture of methanol/water/acetic acid (85/15/0.1%), passes through the column at a rate of 1 ml/min. The mass spectrum determination is carried out according to the selected ion monitoring (SIM) [Di Marzo et al. *Nature* 2001; 410:822-825]. Selected ions correspond to mass/charge values (m/z) of 356 and 348 (molecular ions of deuterated and non-deuterated AEA), 384.35 and 379.35 (molecular ions of deuterated and non-deuterated 2-AG), 304 and 300 (molecular ions of deuterated and non-deuterated PEA), 328 and 326 (molecular ions of deuterated and non-deuterated OEA). The quantity expressed as pmol/mg of lipid extract were compared using ANOVA followed by the Student-Newman-Keuls test.

The maximum reduction of the activity of the palmitoylethanolamide-degrading enzymes (NAAA and FAAH) was also measured using homogenates rat brain membranes [Ueda N et al *Chem Phys Lipids*. 2000 November; 108(1-2):107-21; Tsuboi K. Et al *J Biol Chem.* 2005 March 25; 280(12):11082-92].

Results

The results obtained show that the levels of the cannabinomimetic PEA are significantly higher in HaCaT cells stimulated with Adelmidrol 10 μM (66.4±9.6) compared to basal values (31.6±5.6) (FIG. 1).

No significant variation is observed in the levels of endocannabinoids (AEA, 2-AG) and other cannabinomimetics (OEA) (FIG. 1).

Adelmidrol does not inhibit the activity of catabolic enzymes for PEA (FAAH and NAAA).

| Maximum inhibition of the enzymatic activity (expressed as $IC_{50}$) | Control | Treatment with Adelmidrol 50 μM |
|---|---|---|
| Enzyme FAAH | 21.22 ± 3.18% | 20.15 ± 4.12% |
| Enzyme NAAA | 11.43 ± 1.72% | 11.35 ± 2.26% |

In Vivo Tests in Animals

Osteoarthritis Induced by Sodium Monoiodoacetate

Method

The experiments were conducted using adult male rats of the Wistar strain (weight 200-250 grams) supplied by Harlan Italy, put in enclosures for a week in standard dietary and environmental conditions (temperature 21±1° C., humidity 60±10%, light 12 hours a day and water and food ad libitum) before being used in the experiments. Knee osteoarthritis was induced in rats by a single intra-articular injection of monosodium iodoacetate (MIA) at a dose of 2 mg/25 μL in the infrapatellar area of the right knee, based on the method suggested by Kolbhen but revisited. MIA acts locally by inhibiting glycolysis, destroying the metabolism of chondrocytes and producing cartilage degeneration. At the time of the induction of osteoarthritis, MIA was dissolved in sterile saline. Before carrying out the intra-articular administration, the rats were anesthetized with pentobarbital sodium dissolved in saline at the dose of 60 mg/kg, in an administration volume of 0.2 ml/hg intraperitoneally (i.p.). The animals that received the MIA injection in their right knee represent the osteoarthritic (OA) group. A second group of rats subjected to an intra-articular injection of solvent only in the same right knee is instead the control group.

Behavioral Evaluation of Pain

Evaluation of Mechanical Allodynia

For the measurements of mechanical allodynia (painful response to normally painless stimuli), the Von Frey test (Ugo Basile, Varese, Italy) was used, an instrument consisting of a tactile stimulator that can be moved on a base Perspex platform, a metal grid supported by four columns placed at the corners of the base platform, two compartments further subdivided into which the animals are placed at least 15-30 minutes before the measurement, and an electronic microprocessor. The tactile stimulator is positioned inside an aluminum cylinder provided with a handle that allows the operator to move it on the platform. Inside the cylinder there is an electronic trigger that causes the lifting of a 0.5 mm diameter steel filament, positioned above the cylinder; the activation button of this mechanism is located on both sides of the handle. Thanks to a mirror positioned above the cylinder, alongside the filament, the stimulation can be applied in the correct point of the plantar surface and the movements of the foot can be monitored. The microprocessor is provided with an LCD display that shows the latency time (in seconds) up to the removal of the paw from the mechanical stimulation and the force applied by the filament on the paw (in grams). For measurements in mice, a maximum latency time of 20 seconds and a maximum force corresponding to 5 grams were set.

Evaluation of Knee Edema Through Digital Caliper

Figure 2:
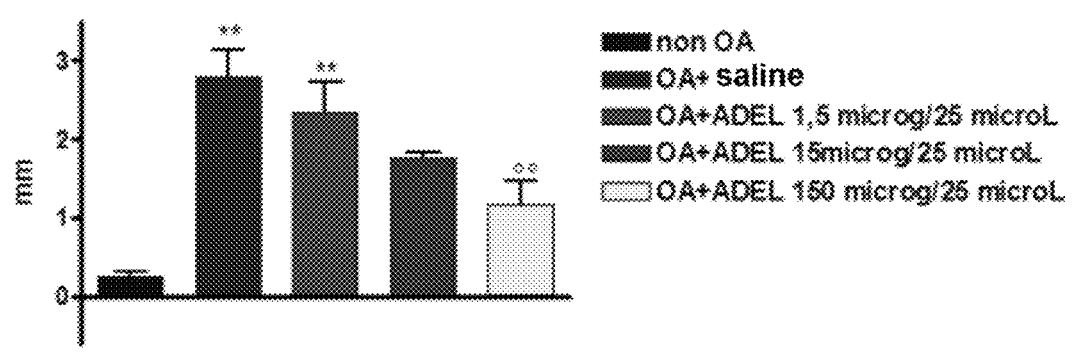
FIG. 2 shows the evaluation of knee edema using a digital caliper—From left to right: non OA: OA+saline; OA+Adelmidrol 1.5 microgr/25 microL; OA+Adelmidrol 15 microgr/25 microL; OA+Adelmidrol 150 microgr/25 microL.

In order to evaluate the formation of the edema in the right knee of the animals after MIA injection, a digital manual slide caliper (measuring capacity 0-150 mm; resolution: 0.01 mm; ROHS Compliant Electronic Digital Caliper—2 Biological Instruments SNC, Italy) was used. The measurement was done manually by evaluating the diameter (expressed in mm) of the left and right knees of each animal at the kneecap. The edema was calculated as the difference between the volume of the right knee and left knee. The data are shown in FIG. 2.

Evaluation of Biochemical Markers

Determination of the Tumor Necrosis Factor (TNF-α) Levels in the Spinal Cord

The determination of TNF-α levels in the synovial fluid was made using an ELISA (Enzyme Linked Immuno-Sorbent-Assay) immunoenzymatic assay using a commercial kit from Biosource International Inc. The method uses a procedure in which the antigen is trapped between two layers of antibodies and for this reason it is called an ELISA sandwich. The sample and the biotinylated antibody are added to the wells of a microtitration plate coated with specific antibodies to TNF-α and the first incubation is carried out, during which the specific cytokine in the sample interacts with both the antigen binding site exposed by the immobilized antibodies on the plate, and with the site of the biotinylated antibody present in solution. After removing the unbound material with a series of washes, the enzyme streptavidin peroxidase is added, which binds to the biotinylated antibody. After a second incubation and subsequent washing to remove the unbound enzyme, a solution containing the substrate (Stabilized Chromogen) is added. Following the enzymatic reaction, a product is generated whose staining intensity is measured spectrophotometrically and is directly proportional to the concentration of TNF-α in the samples.

Results

Treatment

Intra-articular administration of MIA day 0 (T0).
Intra-articular administration of Adelmidrol days 1, 8, 15.
Three doses of Adelmidrol were adopted: 1.5; 15 and 150 µg/injection.

Evaluation of Inflammatory and Pain Parameters

The various parameters are measured at different times in relation to the parameter itself (e.g. inflammatory parameters are evaluated only in the first week since the MIA, pain is always evaluated before and 60 min. after the administration of Adelmidrol).

The results obtained show that Adelmidrol has a strong anti-inflammatory effect, the effect is frankly dose-dependent and evident at all the analyzed times. The regression analysis for the evaluation of the dose response was performed using the area under the curve for each dose used.

Evaluation of the Biochemical Marker TNF-α in the Synovial Fluid

Figure 3:
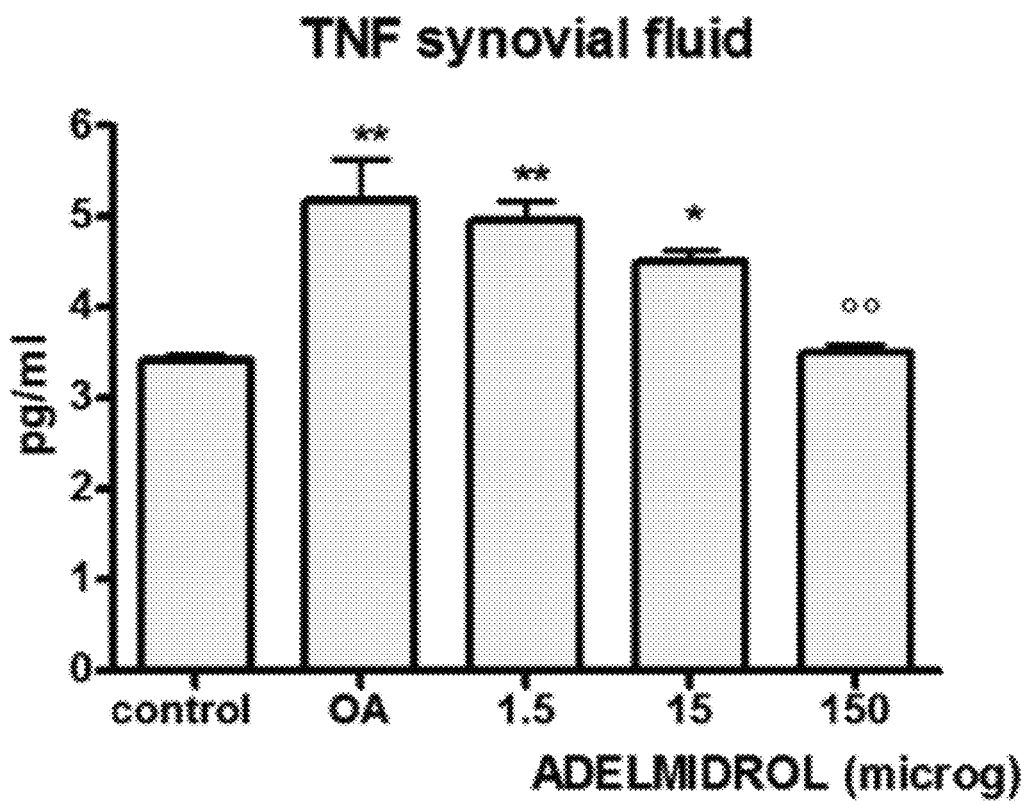
FIG. 3 shows the evaluation of the biochemical marker TNF-α in the synovial fluid.

The effect on edema is accompanied by a reduction in the levels of TNF-α in the synovial fluid (FIG. 3).

In Vivo Tests in Human Beings

Intravesical Instillation in Patients with Painful Bladder Syndrome (BPS)

Method

A sterile solution containing 2% Adelmidrol and 0.1% hyaluronic acid sodium salt was instilled into the bladder of no. 7 female patients through catheter after the complete emptying of the bladder itself. All patients had a confirmed diagnosis of BPS (Bladder Pain Syndrome). Most of the times, the patients had comorbidity with other pelvic diseases (vulvar vestibulitis 4/7; IBS (irritable bowel syndrome) 2/7; Fibromyalgia Syndrome 1/7, Recurrent Urinary Tract Infections (RUTI) 3/7).

Treatments were carried out as attack therapy (one intravesical instillation per week for 8 weeks), followed by maintenance therapy (one instillation per month for 6 months).

Using a dedicated diary, the frequency of urination (measured as the number of urinations in 12 hours), both during the day and at night, and the discomfort with bladder full were controlled, analyzing the pain, the feeling of weight and the burning in the pelvic area (all three parameters were measured by means of numerical scale VAS, before treatment, at the end of the attack therapy and at the end of the maintenance therapy).

Results

The results are shown in the following table.
All the parameters evaluated showed a marked improvement after treatment with Adelmidrol.

|  |  |  | Pat 01 | Pat 02 | Pat 03 | Pat 04 | Pat 05 | Pat 06 | Pat 07 |
|---|---|---|---|---|---|---|---|---|---|
| Patient's age |  |  | 35 years old | 27 years old | 28 years old | 45 years old | 72 years old | 39 years old | 46 years old |
| Treatment | Attack phase |  | 1 instill/ week × 8 weeks | 1 instill/ week × 8 weeks | 1 instill/ week × 8 weeks | 1 instill/ week × 8 weeks | 1 instill/ week × 8 weeks | 1 instill/ week × 8 weeks | 1 instill/ week × 8 weeks |
|  | Maintenance phase |  | 1 instill/ month × 6 months | 1 instill/ month × 6 months | 1 instill/ month × 6 months | 1 instill/ month × 6 months | 1 instill/ month × 6 months | 1 instill/ month × 6 months | 1 instill/ month × 6 months |
| Urination frequency | Before treatment | Day | 8× | 7× | 7× | 8× | 10× | 18× | 12× |
|  |  | Night | 2× | 0× | 1× | 0× | 1× | 6× | 2× |
|  | At the end of attack phase | Day | 6× | 6× | 6× | 7× | 7× | 7× | 7× |
|  |  | Night | 0× | 0× | 0× | 0× | 0× | 1× | 1× |
|  | At the end of maintm. phase | Day | 4× | 5× | 4× | 5× | 5× | 5× | 5× |
|  |  | Night | 0× | 0× | 0× | 0× | 0× | 0× | 0× |

| | | | Pat 01 | Pat 02 | Pat 03 | Pat 04 | Pat 05 | Pat 06 | Pat 07 |
|---|---|---|---|---|---|---|---|---|---|
| Discomfort with bladder full | Pain in the pelvic area | Before treatm. | 9 | 10 | 9 | 7.5 | 9 | 9 | 8.5 |
| | | At the end of attack phase | 4 | 2 | 5 | 2.5 | 3 | 3 | 2 |
| | | At the end of maintm. phase | 3 | 1 | 4 | 2 | 2 | 2 | 1 |
| | Feeding of weight in the pelvic area | Before treatm. | 6 | 8 | 7 | 7 | 6 | 9 | 9 |
| | | At the end of attack phase | 3 | 1 | 4 | 3 | 4 | 4 | 5 |
| | | At the end of maintm. phase | 1 | 1 | 2 | 1 | 3 | 2 | 3 |
| | Burning in the pelvic area | Before treatm. | 6 | 7 | 6 | 6 | 7 | 9 | 9 |
| | | At the end of attack phase | 3 | 0 | 3 | 3 | 4 | 5 | 5 |
| | | At the end of maintm. phase | 2 | 0 | 1 | 0 | 2 | 1 | 1 |

EXAMPLES OF FORMULATION

Example 1

Sterile Solution for Intravesical Instillation

Each 50 ml vial contains:

| | |
|---|---|
| Adelmidrol | 1000 mg |
| Palmitoylethanolamide oxazoline | 500 mg |
| Hyaluronic acid sodium salt | 50 mg |
| Trans-traumatic acid | 50 mg |
| Distilled water | as needed to 50 ml |

Example 2

Sterile Anti-Adhesion Gel for Internal Use

A 500 ml tube contains:

| | |
|---|---|
| Adelmidrol | 15,000 mg |
| Hyaluronic acid sodium salt | 2,500 mg |
| Apyrogenic distilled water | as needed to 500 ml |

Example 3

Dense Solution for Rectal Use

A 10 ml micro-enema contains:

| | |
|---|---|
| Adelmidrol | 200 mg |
| Tocopherol acetate | 5,000 mg |
| Transcutol | 5,000 mg |

Example 4

Viscous Endo-Urethral Solution

A 10 ml single dose squeezable container contains:

| | |
|---|---|
| Adelmidrol | 200 mg |
| Hyaluronic acid sodium salt | 10 mg |
| Trans-traumatic acid | 10 mg |
| Phytosphingosine | 10 mg |
| Usnic acid | 10 mg |
| Polyvinyl alcohol | 20 mg |
| Noveon AA1 | 15 mg |
| Biotin | 1 mg |

Example 5

Sterile Solution for Intra-Articular Infiltration

A 2 ml vial contains:

| | |
|---|---|
| Adelmidrol | 30 mg |
| Palmitoylethanolamide oxazoline | 15 mg |
| Hyaluronic acid sodium salt | 10 mg |
| Phosphate buffer pH 7.0 | as needed to 2 ml |

Example 6

Neuropathic Anti-Itch Spray Solution for Veterinary Use

A 100 ml spray bottle contains:

| | |
|---|---|
| Adelmidrol | 2000 mg |
| Phytosphingosine | 20 mg |
| Trans-traumatic acid | 15 mg |
| Transcutol | as needed to 100 ml |

Example 7

Eye Drops for Application on Corneal Abrasions

Each 1 ml single dose squeezable container contains:

| | |
|---|---|
| Adelmidrol | 25 mg |
| Hyaluronic acid sodium salt | 2.0 mg |
| Trans-traumatic acid | 2.5 mg |
| Sodium chloride | 3.5 mg |
| Monobasic potassium phosphate | 0.5 mg |
| Water | as needed to 1 ml |

Example 8

Gel for Application on Oropharynx Mucosa

Each 250 ml container contains:

| | |
|---|---|
| Adelmidrol | 6,000 mg |
| Palmitoylethanolamide oxazoline | 2,500 mg |
| Sodium carboxymethylcellulose | 5,000 mg |
| Noveon AA1 | 500 mg |

Water with the addition of preservatives as needed to 250 ml.

Example 9

Gel for Corneal Application

Each 10 ml tube contains:

| | |
|---|---|
| Adelmidrol | 100 mg |
| Hyaluronic acid sodium salt | 100 mg |
| Trans-traumatic acid | 10 mg |
| Noveon AA1 | 100 mg |
| Carbomer Ultrez 10 NF | 20 mg |
| Monobasic potassium phosphate | 5 mg |
| Thimerosal | 1 mg |
| Distilled water | as needed to 10 ml |

Example 10

Solution for Spraying with Aerosol

Each 5 ml sterile vial contains:

| | |
|---|---|
| Adelmidrol | 150 mg |
| Distilled water | as needed to 5 ml |

What is claimed is:

1. A method of treating osteoarthritis, the method consisting of:
    administering to a human or animal subject affected by osteoarthritis an effective amount of a combination of Adelmidrol (N—N'-bis(2-hydroxyethyl)nonandiamide) and hyaluronic acid or a salt thereof sufficient to reduce pain sensation in the human or animal; and
    optionally, administering said combination of Adelmidrol and hyaluronic acid or a salt thereof with at least one active ingredient selected from the group consisting of 2-pentadecyl-2-oxazoline of palmitoylethanolamide and trans-traumatic acid;
    wherein the weight concentration of Adelmidrol in pharmaceutical forms for topical application for use in both human beings and animals ranges between 0.2% and 7.0%, and the weight concentration of Adelmidrol in solutions for application on internal epithelia ranges between 0.3% and 5.0%; and,
    wherein the weight concentration of hyaluronic acid for use in both humans and animals is up to 5.0%.

2. The method according to claim 1, wherein said combination of Adelmidrol and hyaluronic acid or a salt thereof are administered in a combined, sequential, or separate manner over a period of time;
    and the method further includes administering said combination with at least one active ingredient selected from the group consisting of 2-pentadecyl-2-oxazoline of palmitoylethanolamide, and trans-traumatic acid.

3. The method according to claim 2, wherein hyaluronic acid and trans-traumatic acid are present in the sodium hyaluronate trans-traumatate double salt form.

4. The method according to claim 1, wherein the amount of Adelmidrol to be administered in the form of solutions intended for the epithelia ranges between 0.5 and 20 mg/Kg body weight.

5. A method of treating osteoarthritis by increasing the endogenous levels of palmitoylethanolamide without inhibiting the activity of the palmitoylethanolamide-degrading FAAH and NAAA enzymes in a human being or animal, the method comprising:
    administering to a human or animal subject affected by osteoarthritis an effective amount of a pharmaceutical formulation or solution containing active ingredients, said active ingredients consisting of:
    a combination of Adelmidrol, hyaluronic acid or a salt thereof and
    optionally, one or more active ingredients selected from the group consisting of
    2-pentadecyl-2-oxazoline of palmitoylethanolamide, and
    trans-traumatic acid;
    wherein the weight concentration of Adelmidrol in the pharmaceutical formulation for topic application for use in both human beings and animals ranges between 0.2% and 7.0%, and the weight concentration of Adelmidrol in the pharmaceutical solutions for application on internal epithelia ranges between 0.3% and 5.0%; and,
    wherein the weight concentration of hyaluronic acid for use in both humans and animals is up to 5.0%;
    wherein such administration of Adelmidrol in said combination causes the palmitoylethanolamide endogenous levels to increase in the human being or animal; and,
    wherein such administration of Adelmidrol in said combination does not inhibit the activity of the palmitoylethanolamide-degrading FAAH and NAAA enzymes in the human being or animal being treated by said combination.

6. The method according to claim 5, wherein hyaluronic acid and trans-traumatic acid are present in the sodium hyaluronate trans-traumatate double salt form.

* * * * *

UNITED STATES PATENT AND TRADEMARK OFFICE
CERTIFICATE OF CORRECTION

PATENT NO. : 11,491,122 B2
APPLICATION NO. : 16/374912
DATED : November 8, 2022
INVENTOR(S) : Maria Federica Della Valle et al.

Page 1 of 1

It is certified that error appears in the above-identified patent and that said Letters Patent is hereby corrected as shown below:

In the Claims

Column 12, Claim 5, Line 42, please correct:
"5.0%; and,"

To:
--5.0%;--

Signed and Sealed this
Twenty-eighth Day of February, 2023

Katherine Kelly Vidal
*Director of the United States Patent and Trademark Office*